(12) United States Patent
Trautwein et al.

(10) Patent No.: US 10,617,381 B2
(45) Date of Patent: Apr. 14, 2020

(54) METHOD AND SYSTEM FOR MEASURING AN X-RAY IMAGE OF AN AREA UNDERGOING MEDICAL EXAMINATION

(71) Applicant: Raylytic GmbH, Leipzig (DE)

(72) Inventors: Frank Thilo Trautwein, Filderstadt (DE); Marcel Dreischarf, Leipzig (DE)

(73) Assignee: Raylitic GmbH, Leipzig (DE)

( * ) Notice: Subject to any disclaimer, the term of this patent is extended or adjusted under 35 U.S.C. 154(b) by 170 days.

(21) Appl. No.: 15/880,021

(22) Filed: Jan. 25, 2018

(65) Prior Publication Data

US 2018/0206812 A1    Jul. 26, 2018

(30) Foreign Application Priority Data

Jan. 25, 2017   (DE) .................. 10 2017 201 164

(51) Int. Cl.
| | |
|---|---|
| *A61B 6/00* | (2006.01) |
| *A61B 6/03* | (2006.01) |
| *G03B 42/02* | (2006.01) |
| *A61B 5/055* | (2006.01) |

(Continued)

(52) U.S. Cl.
CPC .............. *A61B 6/582* (2013.01); *A61B 5/055* (2013.01); *A61B 6/032* (2013.01); *A61B 6/466* (2013.01);

(Continued)

(58) Field of Classification Search
CPC ....... G06T 2207/10116; G06T 2210/41; G06T 7/0012; G06T 11/005; G06T 11/006;

(Continued)

(56) References Cited

U.S. PATENT DOCUMENTS

| | | |
|---|---|---|
| 2011/0268248 A1 | 11/2011 | Simon et al. |
| 2015/0094564 A1 | 4/2015 | Tashman et al. |

(Continued)

FOREIGN PATENT DOCUMENTS

| | | |
|---|---|---|
| DE | 10 2009 008 115 A1 | 9/2010 |
| DE | 10 2012 217 613 A1 | 3/2014 |

OTHER PUBLICATIONS

Oliveira et al., "Medical image registration: a review", Computer Methods in Biomechanics and Biomedical Engineering, 2012, pp. 1-21.

(Continued)

*Primary Examiner* — Ross Varndell
(74) *Attorney, Agent, or Firm* — Muncy, Geissler, Olds & Lowe, P.C.

(57) ABSTRACT

A method for measuring an X-ray image of an area undergoing medical examination that has at least one object. A 3D model is provided of the area undergoing examination that includes a virtual 3D object to be assigned to the object to be measured, a digitally reconstructed X-ray picture is computed based on the 3D model and under the assumption of a virtual projection direction, the X-ray image is compared with the digitally reconstructed X-ray picture, the virtual projection direction is changed relative to the virtual 3D object. The steps of comparing and changing are repeated until a virtual projection direction with maximum correlation between the X-ray image and the digitally reconstructed X-ray picture is found. An object plane is determined that is to be assigned to the virtual 3D object. A corrected projection direction is defined and the X-ray image is measured.

18 Claims, 4 Drawing Sheets

(51) Int. Cl.
*G06T 7/73* (2017.01)
*A61B 90/00* (2016.01)
*G06T 5/00* (2006.01)
*G06T 7/00* (2017.01)

(52) U.S. Cl.
CPC ............ *A61B 6/486* (2013.01); *A61B 6/5217* (2013.01); *A61B 6/5223* (2013.01); *A61B 6/5229* (2013.01); *A61B 90/00* (2016.02); *A61B 90/06* (2016.02); *G03B 42/02* (2013.01); *G06T 5/006* (2013.01); *G06T 7/75* (2017.01); *A61B 2090/061* (2016.02); *G06T 7/0012* (2013.01); *G06T 2207/10081* (2013.01); *G06T 2207/10116* (2013.01); *G06T 2207/10124* (2013.01); *G06T 2207/30012* (2013.01); *G06T 2207/30244* (2013.01)

(58) Field of Classification Search
CPC . G06T 2207/10124; G06T 2207/30008; A61B 2090/367; A61B 6/466; G06K 2209/055
See application file for complete search history.

(56) References Cited

U.S. PATENT DOCUMENTS

2015/0216498 A1* 8/2015 Schulze ............... A61B 6/4085
378/19
2016/0015350 A1 1/2016 Chang
2018/0061090 A1* 3/2018 Jerebko ................ G06T 11/005

OTHER PUBLICATIONS

Bom et al., "Evaluation of optimization methods for intensity-based 2D-3D registration in x-ray guided interventions", 2011, pp. 1-15.
Zheng et al "HipMatch: An object-oriented cross-platform program for accurate determination of cup orientation using 2D-3D registration of single standard X-ray radiograph and a CT volume", Computer Methods and Programs in Biomedicine 95, 2009, pp. 236-248.

* cited by examiner

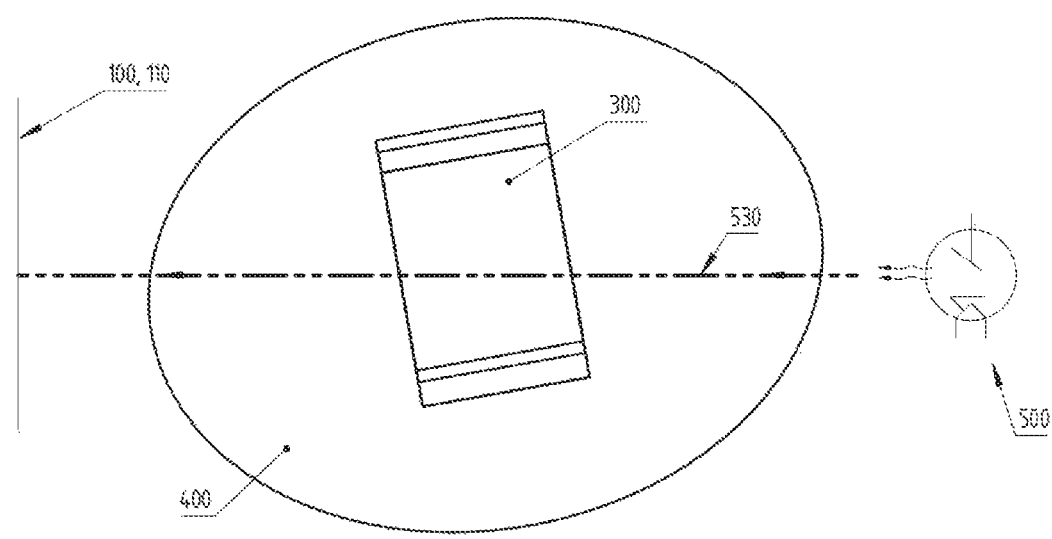
Fig. 1A
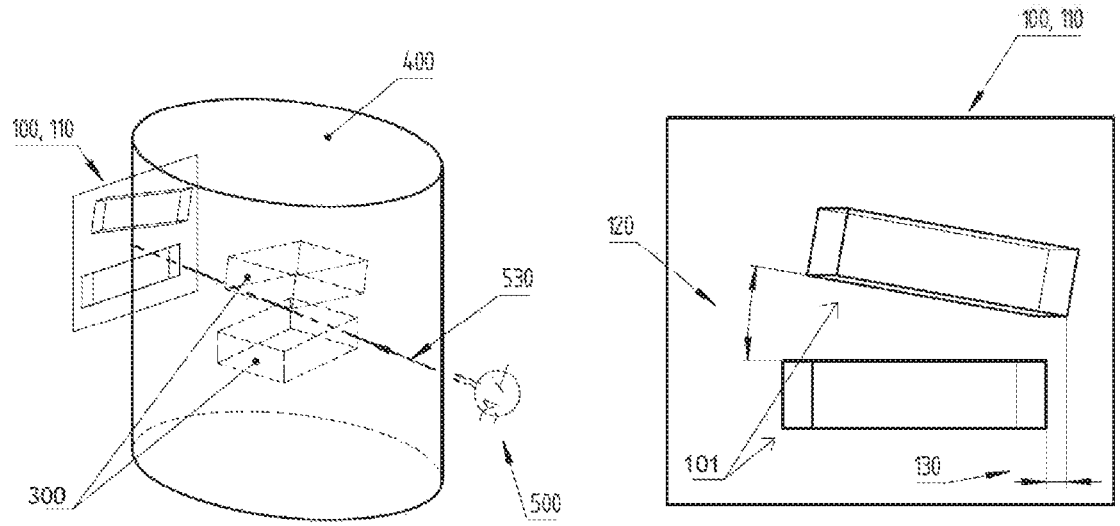
Fig. 1B
Fig. 1C

METHOD AND SYSTEM FOR MEASURING AN X-RAY IMAGE OF AN AREA UNDERGOING MEDICAL EXAMINATION

This nonprovisional application claims priority under 35 U.S.C. § 119(a) to German Patent Application No. 10 2017 201 164.5, which was filed in Germany on Jan. 25, 2017, and which is herein incorporated by reference.

BACKGROUND OF THE INVENTION

Field of the Invention

The invention relates to a method, a device, and a system for measuring an X-ray image of an area undergoing medical examination.

Description of the Background Art

Medical X-ray images are frequently measured for diagnosis, for surgical planning, for producing patient-specific implants, and for quantitative evaluation of the progress of a disease or of a treatment.

Today, primarily computer-assisted methods are available for measuring X-ray images. In practice, however, these methods are limited to the measurement of distances, angles, or surface areas in an X-ray image with the aid of "digital rulers" on the computer screen. For this purpose, usually two structures are identified using appropriate points or landmarks on the screen, are registered with the X-ray image using an input device, e.g., a mouse, and for certain measurements a direction is specified in which the distance measurement is decomposed with regard to its x- and y-components.

In principle, measurements are possible in the same manner on 3D models, but it is necessary to select the appropriate slice plane here. If the measuring plane does not lie in a slice plane predetermined by the imaging device or by the subsequent reconstruction, then the user must define, each time, a plane that differs therefrom using "multiplanar reformation" (MPR). Because of the high radiation exposure caused by a CT scan, the poor imaging of bony structures in MRI scans, and the virtual impossibility of displaying so-called functional images (X-ray images taken in one or more predefined postures) in the 3D modalities, X-ray images are still the first choice of a diagnostic imaging tool for many problems. These functional images are oftentimes prepared for diagnosis and evaluation of the progress of a treatment, and serve to indicate the motion of a second object (such as a vertebral body) relative to a first. To this end, the patient must, for example, bend forward once (flexion), and bend backward for a second image.

Because of minor deviations in the patient's orientation relative to the X-ray machine and internal asymmetries in the objects of interest (for instance, caused by a scoliosis of the spine), in many cases these functional images are not taken exactly at right angles to the vertebral bodies, so that the resulting images each have a different depiction of the same vertebra in consequence. Because of the variability of the X-ray image due to tilting of the image plane ("out-of-plane") relative to the object plane defined by the object or objects to be analyzed, the correct selection of the measuring points in comparative functional imaging is difficult and frequently error-prone.

But even in the case of static, individual shots, it oftentimes is not possible to take X-ray images that are precisely perpendicular and reproducible with respect to the objects to be measured (bones, vertebrae, organs, vessels, tumors) due to errors in positioning the patient or due to pathological deformities (for example, scoliosis).

In consequence, the analysis of clinical image data has until now largely resisted automated analysis and processing. Moreover, tilting leads to a distortion of angles and a shortening of measured distances as compared to the actual distances, so that a large number of the measurements on radiological images are of only limited value for diagnostic and statistical purposes or for the preparation of patient-specific implants. The sizing or matching of implants to morphological conditions is frequently impossible using 2D images, and requires 3D imaging with more resource-intensive reconstruction and planning by the user.

SUMMARY OF THE INVENTION

It is therefore an object of the present invention to provide a method, a device, and a system for measuring X-ray images of an area undergoing medical examination that at least partially avoid the aforementioned disadvantages.

In an exemplary embodiment, the method, device, and system according to the invention is designed for measuring an X-ray image of an area undergoing medical examination that has at least one object. According to the invention, the method includes the following steps: providing a 3D model of the area undergoing examination, which model has a virtual 3D object to be assigned to the object; computing a digitally reconstructed X-ray picture on the basis of the 3D model and under the assumption of a virtual projection direction; comparing the X-ray image with the digitally reconstructed X-ray picture; changing the virtual projection direction relative to the 3D object; repeating the comparing and changing steps until a virtual projection direction is found in which there is maximum correlation between the X-ray image and the digitally reconstructed X-ray picture; determining an object plane to be assigned to the 3D object; defining a corrected projection direction and an associated output plane, wherein the output plane has a known orientation with respect to the object plane determined, wherein the output plane is oriented orthogonally to a corrected projection direction; and measuring the X-ray image, taking into account the deviation between the corrected virtual projection direction and the virtual projection direction determined.

With the aid of the invention, it is possible to exactly measure two-dimensional medical images of human organs, vessels, tumors, or bones that were not taken orthogonally, which is to say not exactly along or perpendicular to an axis or plane of symmetry of the object of interest or its immediate surroundings.

An area undergoing medical examination can be any area of the human (or animal) body. An object contained by the area undergoing examination can in principle be any sub-region of the area undergoing examination. For example, an object can be a bone, vertebra, organ, vessel, or tumor, or can be composed in each case of a subsection of the aforementioned elements.

An X-ray image of the area undergoing medical examination is a depiction of the examined area obtained with the aid of an X-ray device, wherein the depiction has a (real) projection direction and a (real) image plane, which normally is oriented orthogonally to the projection direction. The position of the image plane is defined by, for example, the position of the X-ray detector or film cassette of the X-ray device. The X-ray image can be present in digital form or can be converted into a digital form.

A digital, reconstructed X-ray picture can be obtained through a simulation in which a virtual projection direction and a virtual image plane are assumed, wherein the virtual image plane preferably is oriented orthogonally to the virtual projection direction.

A 3D model of the area undergoing medical examination constitutes a virtual, three-dimensional representation of the area undergoing medical examination. The 3D model includes the 3D object, wherein the 3D object constitutes a virtual, three-dimensional representation of the object.

According to an embodiment of the invention, an object plane is determined that is to be assigned to the 3D object. The real object also has a corresponding object plane. The object plane is preferably oriented such that an X-ray image taken at right angles to the object plane provides measurement results with high accuracy. The precise orientation of the object plane generally depends on the type of object being examined and on the type of measurement results desired. Usually, the object plane is arranged symmetrically within the object. The orientation of the object plane can be determined through morphological features (edges, surfaces, planes of symmetry) of the object. If, for instance, the length of a vertebral body is to be measured in the anterior-posterior direction, then the object plane can extend through the center of the vertebral body as a plane of symmetry (ideally corresponding to the sagittal plane of the human body).

The present invention utilizes the fact that 3D images of an area undergoing examination and of the object of interest are oftentimes prepared during the course of diagnosis or treatment by means of computed tomography (CT) or magnetic resonance imaging (MRI). The 3D model and the 3D object contained therein can be created from these 3D images. Alternatively, the 3D model and/or the 3D object can be generated through a mathematical, three-dimensional, discrete description of one or more of the objects of interest, wherein the 3D objects are positioned in the (shared) 3D model. Preferably, the 3D model and/or the 3D objects are provided with physical properties for calculating the attenuation of a (virtual) X-ray beam penetrating the 3D model or the 3D objects.

The 3D model that is provided is then used for calculating the digitally reconstructed X-ray picture, wherein the virtual projection direction is changed until maximum correlation exists between the X-ray image and the digitally reconstructed X-ray picture. The term "maximum correlation" does not mean that absolute or complete agreement is required. It can suffice if there is agreement to a desired degree. The determination of maximum correlation is also referred to hereinbelow as 2D-3D registration.

In other words, what is carried out via the maximum correlation is a solution to a mathematical optimization problem. The degree of correlation between the images is computed e.g. into a single value, which changes as the direction of the projection changes. A goal is to find the direction of the highest correlation of the projected image with the reference image, which would be denoted by the highest value of the correlation coefficient. As there is no closed solution that can be computed, the maximum correlation has to be found. For example, the direction is modified in steps of, e.g., 20° for all combinations of the spatial directions)(3×360°. Then a combination with the highest correlation coefficient and the step-size is varied in, e.g., 5° in a smaller window (e.g. 3×+/−15° of the previously found solution). This procedure could go on forever with always smaller increments, but at some point there is no additional reasonable technical benefit to optimize it further so the optimization is aborted. In other words, the optimum is sought, but the search may be aborted if certain requirements are met (e.g. a certain step width, or a negligible change of the correlation coefficient between a certain number of iterations).

Also, the correlation can be mathematically expressed in a way that the optimum can be either a value as high as possible, as close as possible to a given number (e.g. 1), or it can be as low as possible, or as close as possible to zero (or any other number). Also, more than one correlation coefficient could be defined, where the goal would be to minimize all coefficients for the best (reasonably) possible maximum correlation.

It is noted that the above description is a bit simplified because in an exemplary embodiment, not only all three angular directions are varied for the projection, but also the position of the object within the x-ray machine and even the geometry of the machine (distance between x-ray source and detector) to make the virtual image appear exactly as the real image. This multi-variable optimization problem is discussed in further the publication "Medical image registration: a review" by Francisco P. M. Oliveira and Joaˉo Manuel R. S. Tavares, Instituto de Engenharia Mecaˆnica e Gestaˉo Industrial, Faculdade de Engenharia, Universidade do Porto, Rua Dr. Roberto Frias, 4200-465 Porto, Portugal or in the publication "Evaluation of optimization methods for intensity-based 2D-3D registration in x-ray guided interventions," by I. M. J. van der Boma, S. Kleinb, M. Staringc, R. Homand, L. W. Bartelse, and J. P. W. Pluime, which are both herein incorporated by reference.

Because the invention performs a 2D-3D registration in addition to determining an object plane of the 3D object of interest, the X-ray image can be measured in an especially simple and exact manner by the method according to the invention.

This is achieved by defining the corrected projection direction and the associated virtual output plane, which stands in a known orientation to the object plane determined. Especially when the real X-ray image was taken at an angle that is not exactly orthogonal to the object plane, the method provides a corrected projection direction that is oriented to the object plane as well as an associated output plane that allows a corrected measurement of the X-ray picture.

The essence of the invention is thus the correction of two-dimensional medical X-ray images (for example, of vessels, tumors, or bones) that were not taken orthogonally, which is to say not taken exactly along or perpendicular to an axis or plane of symmetry of the object of interest or its immediate surroundings, thereby hindering precise measurement of the object. A 3D model that contains at least one of the objects of interest is used for correction of the two-dimensional image. Preferably, the 3D model is used as the basis for defining an object plane and for determining the tilt of the image plane (or of the uncorrected projection direction) relative to the object plane. With this information, the measurement of any distances, angles, or areas in the original image can be corrected, or alternatively, a digitally reconstructed image based on the geometric 3D model, modified if applicable, can be generated in the desired object plane.

The method according to the invention thus makes it possible to perform measurements of angles, distance, and area on potentially "tilted" X-ray images with high precision, wherein the effort for manual user interaction is low. On individual X-ray images, absolute measurements of distance dimensions are possible with high precision by the means that the known absolute scale of the 3D model (voxel/mm) can be projected onto the reconstructed X-ray picture and/or the original X-ray image (100) (pixel/mm).

Moreover, the method can be carried out with a plurality of X-ray images so that comparative relative measurements can be performed on multiple X-ray images. In this case, a distance dimension is preferably referenced to the distance in another object of another X-ray image, and the ratio is specified.

Preferably, the output plane is oriented parallel to the determined object plane. This is equivalent to the corrected projection direction being oriented at right angles or substantially right angles to the object plane.

Alternatively, the output plane can also be oriented parallel to a principal plane of a coordinate system predefined by the 3D model or by the 3D object. This is especially advantageous when the 3D model was produced with a recumbent patient, since in this case the patient is already oriented nearly optimally and reproducibly for many measurement tasks during the creation of the 3D model or 3D objects, so the object planes of the 3D objects are already in an optimum orientation relative to the 3D model.

In an embodiment, the step of measuring the X-ray image includes determining a correction function that results from the deviation between the corrected virtual projection direction and the projection direction determined, and/or applying the correction function to the measurement results obtained.

In this case, therefore, a measurement can be made directly on the (real) X-ray image, wherein any measuring inaccuracies that have resulted from a tilting of the object plane relative to the real projection direction during creation of the X-ray image are corrected by the correction function according to the invention.

Alternatively, provision can be made that a corrected, digitally reconstructed X-ray picture in the output plane is generated on the basis of the corrected virtual projection direction, wherein the X-ray image is measured using the corrected, digitally reconstructed X-ray picture in the output plane. The measurement in this case can be made directly on the digitally reconstructed X-ray picture, which is projected into the output plane using a corrected projection direction.

Preferably, the measuring includes the measurement of a distance between measuring points, the measurement of an angle between measuring lines, and/or the measurement of a surface area of measuring areas.

Provision can be made that the 3D object is obtained by a method for three-dimensional imaging, in particular by computed tomography or magnetic resonance imaging. In this case, the object plane can be determined on the basis of the 3D object using gray-scale intensities assigned to the 3D object. Preferably, the virtual object plane is determined on the basis of an optimization, in particular a least squares optimization, of the distance between points, lines, curves, or planes, and a selection of voxels of the 3D object, and/or on the basis of edges or surfaces of the 3D object, and/or with machine learning methods, especially with trained neural networks.

Alternatively, the 3D object can be based on a computer-generated geometry description, for example on a "statistical shape model," an "active appearance model," or an "active shape model." In this case, the method according to the invention can even be carried out when there are no three-dimensional images of the area undergoing examination.

Provision can be made that the virtual object plane is determined on the basis of landmarks associated in advance with the 3D object.

In this case, provision can be made in step d. that the 3D object is additionally modified through local and/or elastic deformation. Here, the term local deformation refers to a modification in a subregion of the 3D object. An elastic deformation refers to the change in the shape of the 3D object with the aid of elastic models in which the 3D object is modeled, for example as an elastic or viscous liquid. In this way, a registration between the 3D object and the X-ray image can take place, even when there are complex (local) distortions. A local and/or elastic deformation differs in this regard from an affine transformation, in which a rigid 3D object is merely moved and aligned.

The method according to the invention can also be used in the case of an area undergoing examination that includes at least two objects, wherein preferably the virtual projection direction is kept constant, and the positions and/or orientations of the 3D objects (300') relative to one another are changed within the 3D model, wherein the steps of comparing and changing are repeated until the position and/or the relative orientation for each 3D object is found in which there is maximum correlation between the X-ray image and the digitally reconstructed X-ray picture. A virtual object plane that is to be assigned to the majority of 3D objects is determined, and whereby the positions of the 3D objects determined within the 3D model and/or the orientations of the 3D objects relative to the corrected projection direction are taken into account.

The measuring step can include the measurement of a distance between two measuring points and/or the measurement of an angle between two measuring lines, wherein the two measuring points and/or measuring lines preferably are to be assigned to different 3D objects.

In an advantageous embodiment, a scale of length of the 3D model is transferred to the X-ray image. This is especially advantageous since X-ray images frequently are uncalibrated with respect to a scale of length, but the 3D model has a calibrated scale. Consequently, a calibrated measurement directly on the X-ray image is made possible in a simple way.

In addition, a device is provided for carrying out the method according to the invention, comprising: a memory, in which a 3D model of the area undergoing examination is stored, wherein the 3D model has a virtual 3D object to be assigned to the object; a computing module, which is designed to compute a digitally reconstructed X-ray picture using the 3D model and under the assumption of a virtual projection direction; a comparison module for comparing the X-ray image with the digitally reconstructed X-ray picture; a change module, which is designed to change the virtual projection direction relative to the 3D object and/or to change the positions of the 3D objects within the 3D model and/or the orientations of the 3D objects relative to one another and/or the shape of the 3D objects; a geometry module, which is designed to determine a virtual object plane to be assigned to the 3D object and to define an output plane that has a known orientation to the object plane and that is oriented orthogonally to a corrected projection direction; a measurement module for measuring the X-ray image, taking into account the deviation between the corrected virtual projection direction and the virtual projection direction determined and/or taking into account the positions of the 3D objects within the 3D model determined and/or the orientations of the 3D objects relative to the corrected projection direction.

Also, a computer program is provided for measuring an X-ray image of an area undergoing medical examination, which program contains computer program code for carrying out the method according to the invention.

The computer program can be stored on a machine-readable medium (computer program product) or a non-transitory computer readable media.

Also, An X-ray measuring system is provided that includes an X-ray source that emits X-radiation along a projection direction onto an area undergoing examination, an X-ray detector detecting an X-ray image produced in an image plane, a memory adapted to store a 3D model of the area undergoing examination, the 3D model including a virtual 3D object to be assigned to the object, and a display, wherein a digitally reconstructed X-ray picture is computed using the 3D model and based on a virtual projection direction wherein the X-ray image is compared with the digitally reconstructed X-ray picture. The virtual projection direction is changed relative to the virtual 3D object or wherein a position of the virtual 3D object within the 3D model or an orientation of the virtual 3D object or a shape of the 3D object is changed. A virtual object plane that is to be assigned to the virtual 3D object is determined. An output plane is defined that has a known orientation to the object plane and is oriented orthogonally to a corrected projection direction, and wherein a measurement result is determine based on the X-ray image measured based on a deviation between the corrected virtual projection direction and the virtual projection direction determined or the position of the virtual 3D object within the 3D model determined or the orientation of the virtual 3D objects relative to the corrected projection direction, and the measurement result is provided on the display or another user readable medium.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1A shows a top view of an area undergoing medical examination with slightly tilted orientation relative to a projection direction during a process known from the prior art for producing an X-ray image;

FIG. 1B is a perspective view of FIG. 1A;

FIG. 1C is an illustration of an X-ray image obtained using the arrangement from FIGS. 1A and 1B;

DETAILED DESCRIPTION

Figure 2:
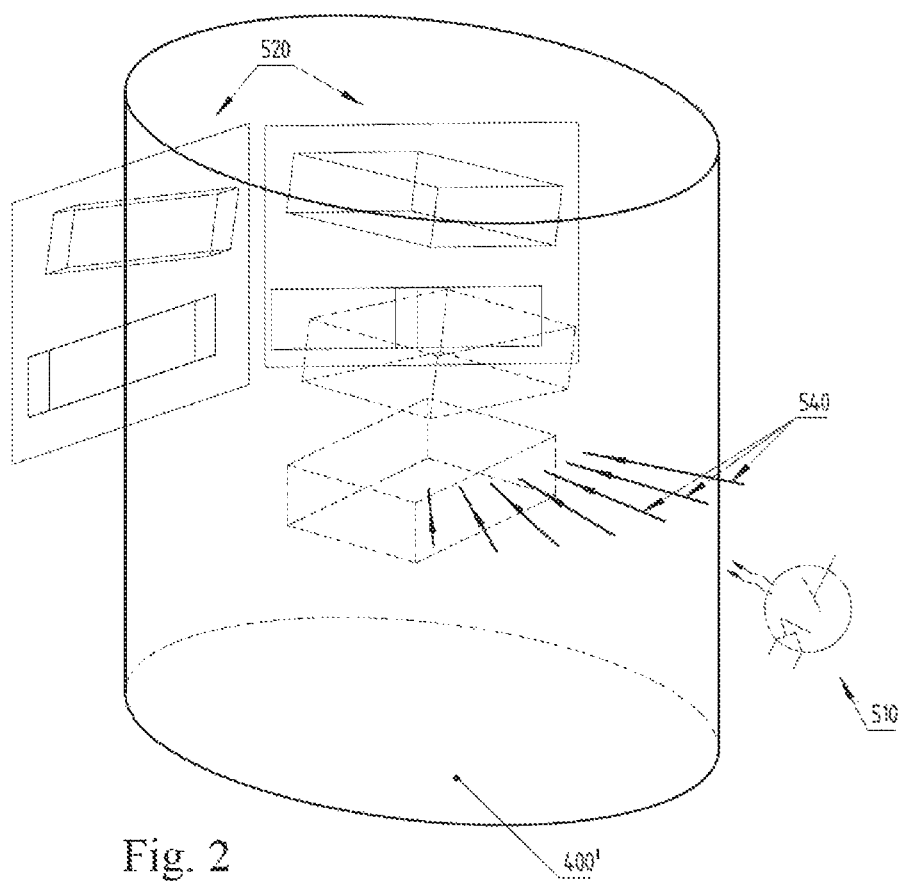
FIG. 2 is an illustration of the method of 2D-3D registration from different projection directions.

FIGS. 1A to 1C illustrate a method known from the prior art for producing an X-ray image. FIG. 1A shows an X-ray source 500, which emits X-radiation along a projection direction 530 onto an area 400 undergoing medical examination, with an X-ray image 100 being produced in an image plane 110. The area 400 undergoing examination has an object 300, which can take the form of, for example, a vertebral body, with a plane of symmetry of the object 300 being tilted relative to the projection direction 530.

FIG. 1B shows a perspective view of FIG. 1A, where it can be seen that the area 400 undergoing examination has two objects 300.

FIG. 1C shows an enlarged view of the X-ray image 100 in the image plane 110. In addition, an angular measurement 120 between the two objects and a distance measurement 130 are also included in the illustration. Because of the tilting of the objects 300 relative to the projection direction 530, the image 101 of the objects 300 in the X-ray image 100 projected in the image plane 110 has so-called "double edges." In practice, this leads to a blurred representation of the object outlines on the X-ray image 100. The angular and distance measurements are thus subject to a measurement error.

With the aid of a device according to the invention, and applying the method according to the invention, the X-ray image 100 can be measured as described below.

An exemplary device for carrying out the method according to the invention can have, for this purpose, a memory, a computing module, a comparison module, a change module, a geometry module, and a measurement module. The elements of the device according to the invention can be composed of a computer on which the software according to the invention is executed. The computer can include a microprocessor, a working memory, and a nonvolatile memory or an I/O interface to an external, nonvolatile memory. It is noted that the above modules can also be distributed within, for example, a network, such that the measurement module may reside on a computer at a remote location.

In an especially advantageous embodiment, the microprocessor is suitable for highly parallelized code execution (e.g., a graphics processor), and the working memory is connected to the microprocessor as directly as possible and with the highest possible bandwidth (e.g., the RAM of a graphics card).

In an exemplary embodiment of the method according to the invention, first a 3D model 400' of the area undergoing medical examination is provided in the memory, which model corresponds at least partially to the area 400 undergoing medical examination. For purposes of simplicity, application to just one X-ray image 100 is described below, but the method can be applied equally well to multiple X-ray images 100, such as are produced with stereoscopic or biplane imaging, for example.

Next, if the complete image contents are not being compared, the relevant areas in the X-ray image 100 and/or of the 3D model 400' can be defined. To this end, an optional selection module may be present. If multiple objects 300 that can move relative to one another are to be measured, a positional deviation of the 3D objects relative to one another between the X-ray image 100 and the 3D model 400' may come about due to different orientations of the patient (for example, standing vs. lying down) or a time interval. In this case, the selection module can be used to make an association between the objects 300 depicted on the X-ray image 100 and the 3D objects 300' contained in the 3D model 400'.

Subsequently, digitally reconstructed X-ray pictures (DRR) 520 of the 3D model 400' or of the 3D objects 300' of the patient are computed from different projection directions 540 with the aid of the computing module, using the 3D model 400' and, if applicable, the objects or areas that were selected beforehand. This is accomplished in the exemplary embodiment with the aid of a virtual X-ray source 510 and a physical-mathematical description of the X-ray beam attenuation of a 3D model penetrated by X-ray beams, as well as a projection plane at which the radiation remaining after attenuation through the body is computed in a discretized manner and represented in gray-level values.

Figure 3:
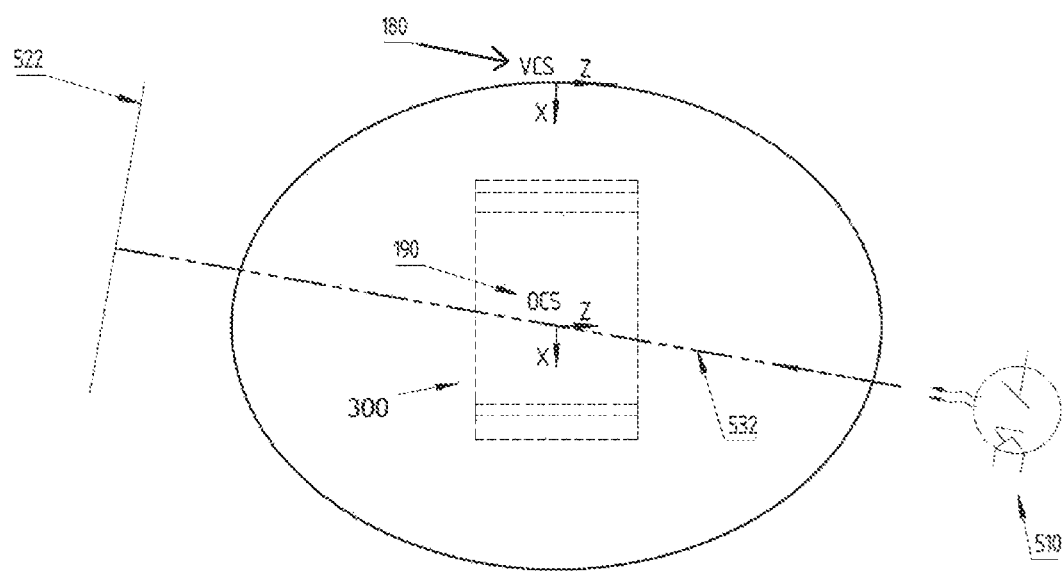
FIG. 3 is an illustration of a resultant digitally reconstructed X-ray image, the projection direction of which corresponds to the projection direction of the uncorrected X-ray image.

In a comparison module, the similarity of the digitally reconstructed X-ray pictures (DRR) 520 is evaluated for the selected image sector of the X-ray image 100. The change module can then vary the projection direction as compared to the 3D model 400' and/or as compared to the 3D objects 300' until maximum correlation exists between a digitally reconstructed X-ray picture (DRR) 520 and the X-ray image 100, using an optimization algorithm, for example. This uncorrected projection direction 532 found in this way provides an uncorrected, digitally reconstructed X-ray picture 522, which corresponds to the X-ray image 100 in the image plane (110). The process described above is shown purely by way of illustration in FIGS. 2 and 3. FIG. 2 depicts, in a hypothetical perspective view, a virtual X-ray source 510 that generates a multiplicity of DRRs 520 with the aid of different projection directions 540. FIG. 3 shows the subject of FIG. 2 in a hypothetical top view, wherein the uncorrected projection direction 532 that was determined is shown, and the resultant uncorrected DRR 522 is indicated. In addition, it can be seen that the uncorrected projection direction 532 is tilted relative to a plane of symmetry of the object 300' and also relative to an object coordinate system 190 of the object 300'.

If multiple areas are defined, the above-described step can be repeated for each area in order to be able to average the uncorrected projection direction 532 over all the areas rather than at just one area. The uncorrected projection direction 532 thus determined as compared to the 3D model 400' or as compared to the 3D objects 300' corresponds to the real projection direction that was used in the creation of the X-ray image, wherein the real projection direction is oriented orthogonally to the image plane 110 of the X-ray image 100.

If the 3D model 400' is based on a synthetic description of the 3D objects 300', for example through a computer-generated "statistical shape model" (SSM), "active appearance model" (AAM), or an "active shape model" (ASM), then the geometry description is present in the shape of discrete area or volume elements. This model can be adapted to the actual morphology of the patient independently of the preceding steps. For many applications, the X-ray image 100 is already sufficient for this purpose. If additional X-ray images 100 from other projection directions are available, they can likewise be used for adapting the mathematical geometry descriptions and improving the imaging precision of the 3D objects 300'. The creation of a patient-specific 3D model 400' with patient-specific 3D objects 300' on the basis of statistical shape models and X-ray images has been described, for example by Zheng et. al. in "Scaled, patient-specific 3D vertebral model reconstruction based on 2D lateral fluoroscopy," Int J CARS (2011) 6:351-366, and is not essential to the invention.

The method according to the invention is likewise suitable for the case in which the measurement task concerns determination of angles or distances between multiple objects 300 that can move relative to one another, for example between vertebrae of the spinal column. In this case, in an additional step, the (segmented, if applicable) 3D model 400' is iteratively adapted for each 3D object 310 through an affine transformation of the 3D objects 300' with the above-described 2D-3D registration. However, now the projection direction is not varied, but instead the position and orientation of the 3D objects 300' are varied until the DRR generated after each change achieves the best possible agreement with the X-ray image 100. Preferably, it is possible to enter constraints through an interface, for example with regard to the maximum translation or rotation, in order to significantly restrict the search space so that this adaptation can take place in very little computing time. After completion of the adaptation, the defined sectors or the entire X-ray image 100 of the objects 300 and the DRR for the as-yet uncorrected orientation 522 have a maximum possible agreement. The 3D objects 300' are thus correctly arranged within the 3D model 400' with respect to one another and to the image plane 110.

If X-ray images that were taken simultaneously from different acquisition directions are available (stereo or biplane images), these X-ray images 100 are suitable for especially precise transformation and arrangement of the 3D objects 300' in the 3D model 400' according to the above-described method.

In another step, the output plane 600, which corresponds to the actual measuring plane that is desired, is then determined with the aid of the geometry module. In a first variant, this plane can be a plane of the volume coordinate system (180) (VCS) of the 3D model 400' (see FIG. 3). This is especially advantageous when the 3D model 400' or 3D object 300' already has an optimum and reproducible orientation, for example when the 3D model 400' was produced from an MRI or CT image with a recumbent patient, which in this case is already oriented nearly optimally and reproducibly for many measurement tasks.

Figure 4:
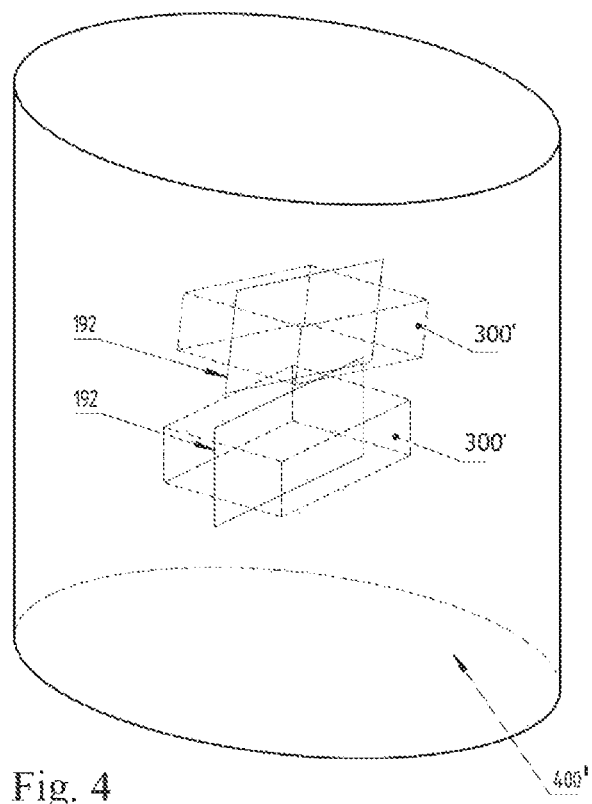
FIG. 4 is a representation of the 3D objects and object planes within the 3D model.

An advantageous embodiment is the automatic determination of the output plane 600, or of a measurement coordinate system 610 corresponding to the output plane, based on the definition of the object coordinate system 190 (OCS) or of the object plane 192 (see FIGS. 3 and 4). To this end, the object coordinate system 190 or the object plane 192 is first determined with the aid of the method according to the invention. Exemplary object planes 192 of the 3D objects 300' within the 3D model 400' are shown in FIG. 4. The determination can advantageously be accomplished through an analysis of the gray-level value information of the 3D objects 300'. As a result, definition on the basis of the actual location and position of the relevant 3D objects 300' is possible, especially when there is an asymmetrical arrangement of internal organs or bones. The selection of the voxels used for determination of the object plane 192 or of the object coordinate system 190 can be limited manually or programmatically to this end. This can be achieved through one or more of the following methods, depending on the structure to be identified: a) limitation of the permissible range of gray level values of the voxels; b) definition of one or more selection areas through the X-ray image 100; c) using machine learning methods (neural networks); d) definition of one or more slice planes through the X-ray image 100 or e) through the 3D model 400'. If the selection of the areas or slice planes is to be done manually, this preferably takes place in the as-yet uncorrected X-ray image 100, wherein the selection is projected through the uncorrected projection direction 532 into the 3D model 400' and only the voxels that remain due to the slice plane, selection areas, gray levels, and other limitations are selected. This selection can be made manually by the operator or programmatically.

Points, lines, ellipses, planes, or other analytically describable contours, collectively referred to as reference objects, are suitable for defining the object plane 192 or the object coordinate system 190. The position and shape of the reference objects within the 3D model 400' can be determined in particular I) using centroid or (center of area) considerations; II) regression methods such as minimization of the squares of the distance from voxels to the reference objects; III) using symmetry considerations or IV) using trained neural networks in conjunction with two-dimensional or three-dimensional geometry descriptions (e.g., AAM, ASM, SSM). Depending on the measurement task or object, the reference objects can also be arranged into templates that can be dragged manually or automatically onto the visible structures and adapted.

If the measurement coordinate system or the output plane 600 is defined on the basis of the 3D objects 300', it can be advantageous—depending on the nature of the task—to do this on the basis of the object coordinate system 190 or the object plane 192 of a single 3D object 300, or on the basis of multiple 3D objects 300. If multiple 3D objects 300 are used for definition, the position of the output plane 600 or of the measurement coordinate system is expediently defined by averaging of the individual object planes 192 or object coordinate systems 190 of the individual 3D objects 300, e.g., by the relevant angle bisectors between the direction vectors. In another preferred variant, the measurement coordinate system or the output plane 600 is defined on the basis of both objects (e.g., through the axis of symmetry of a superior vertebral body and the midpoint of an inferior vertebral body).

A similarly advantageous variant for definition of the output plane 600 or of the measurement coordinate system is in utilizing predefined nodes of a mathematical 3D model 300', for example of an ASM, AAM, or SSM. Thus, the output plane 600 can be completely described through three characteristic points. If the points simultaneously define origin and two axes, it is even possible to define the output coordinate system with only three points.

Figure 5:
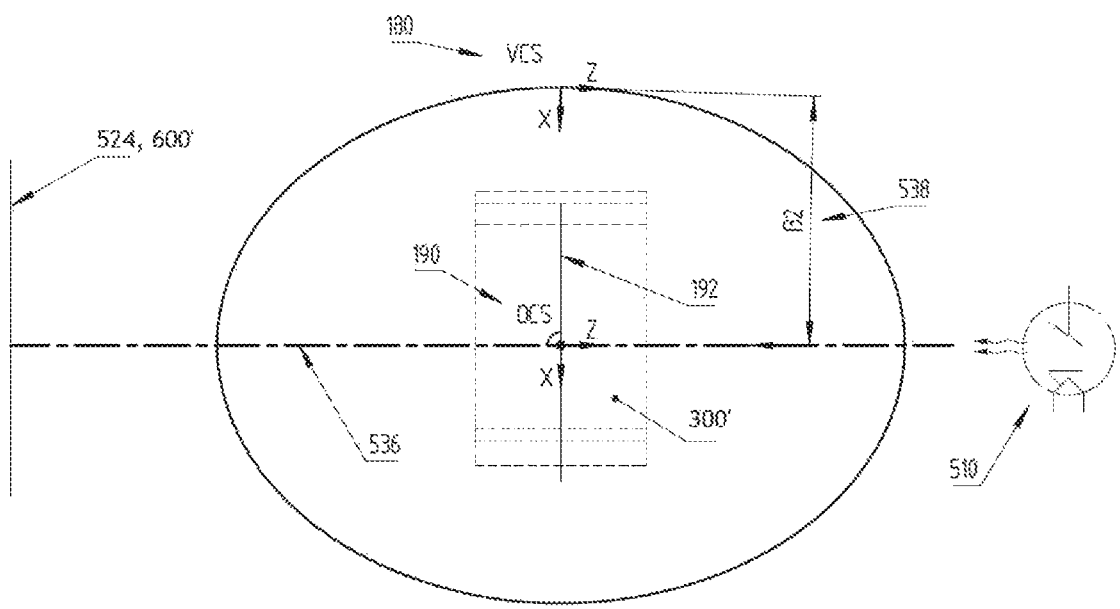
FIG. 5 is an illustration of the corrected digital reconstruction of the X-ray picture in the output plane.

If the measurement coordinate system or the output plane 600 is defined using one of the above-described methods, then the orientation of the corrected projection direction 536 is simultaneously defined as the normal vector of the output plane 600 or through the use of the Z-axis of the measurement coordinate system. FIG. 5 illustrates the corrected projection direction (536) that is oriented orthogonally to the object plane 192 of the 3D object 300' and that provides a corrected DRR 524 in the output plane 600.

Figure 7:
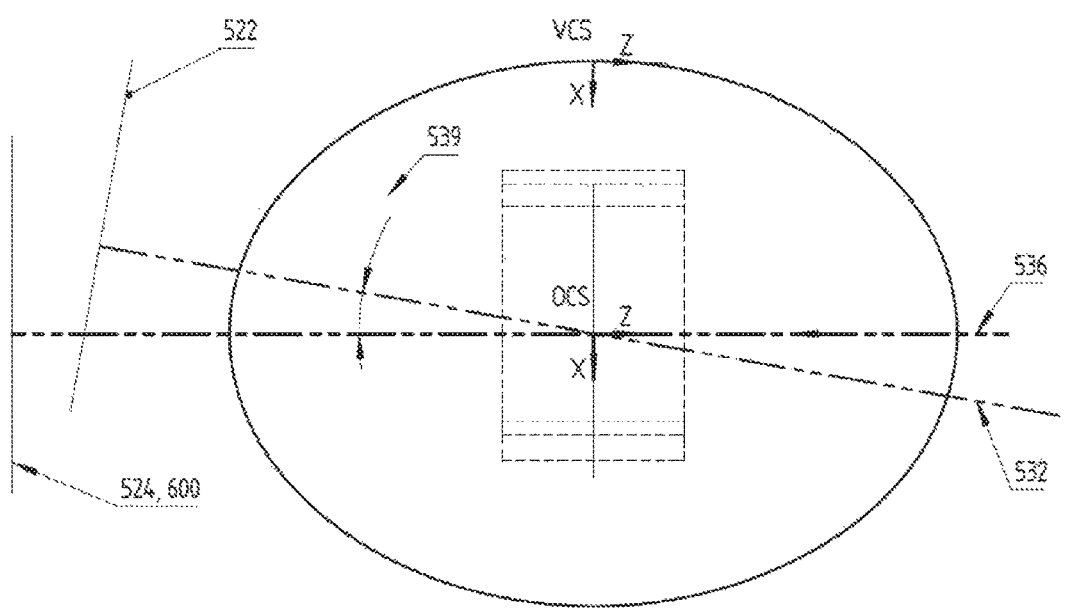
FIG. 7 is an illustration of the determination of the angle of tilt or of the differential angle between uncorrected and corrected projection directions.

Now, once the alignment of the X-ray image 100 is known through the simulation of the DRR 522 of the uncorrected orientation 532, and the orientation of the output plane 600 or the measurement coordinate system is also known, then in a further step the tilt can be determined as the difference between the alignment of the X-ray image 100 and the corrected output plane 600. This tilt results from the deviation between the corrected projection direction 536 and the previously determined uncorrected projection direction 532. The process of determining a deviation between the projection directions 536 and 532 is illustrated in FIG. 7. The deviation can be measured in the form of a differential angle 539. The measurement module according to the invention can be designed to determine the deviation for this purpose.

Before the actual measuring, a definition of the measuring points for distance measurement, the lines for angular measurement, or the surfaces for area measurement can take place in an optional additional step. If the distance or angular measurement is to relate to a specific direction, then this direction, and thus the measurement coordinate system, must likewise be defined (if this has not already been done). This definition can take place: a) on the basis of the uncorrected X-ray image 100; b) in a more advantageous embodiment, on the basis of a corrected DRR 524, which is projected into the output plane 600; or c) through predefined nodes of the mathematical 3D object description, for example for distance measurement 160 in ASM, AAM, or SSM.

The advantage of variant b) is the always perpendicular or uniform imaging of the structures under examination, which simplifies the manual or automatic placement of landmarks. Automatic placement of landmarks can preferably take place by means of the above-described methods for definition of the object coordinate system. The advantage of variant c) is that the "nodes" need only be connected once in advance with the points or constraints defining the measurement coordinate system, and thereafter the measurement coordinate system is automatically oriented to the appropriate geometry of the 3D object or objects 300' for every measurement.

If output of the measured values is to take place in a unit of length, e.g., for distance measurements, the X-ray image 100 or the corrected DRR 524 must be calibrated to a scale of pixels/unit of length. This can be accomplished on the basis of a calibration object with known dimensions that is visible in the X-ray image 100, or through transfer of the scale of the 3D model (voxels/unit of length), which is known as a rule. If the 3D model includes an ASM or SSM, the size of the model is always one of the vectors with high variability. In this case, the calibration of the X-ray image, the corrected DRR 524 in the output plane, or the ASM/AAM/SSM must take place on the basis of a calibration object with known dimensions that is visible in the X-ray image 100. When requirements for accuracy are less stringent, it is possible to resort to statistical morphological data of visible objects or the approximate scale of the X-ray image 100, which is usually contained in the file of the X-ray image.

Angular measurements usually require no calibration to a unit of length, so this step can be omitted for measurement tasks that require only angular measurements.

Figure 6:
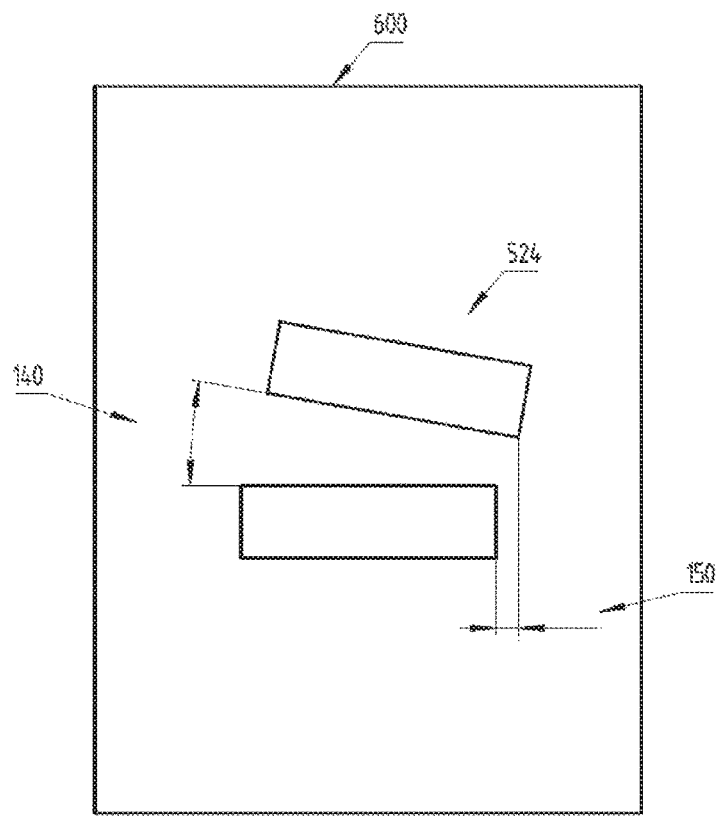
FIG. 6 is an illustration of a corrected digitally reconstructed X-ray picture in the output plane.

The actual measurement can then take place in an additional step with the aid of the measurement module using the corrected projection direction 536 in the corrected DRR 524 in the output plane 600. This is illustrated in FIG. 6. It is evident from the figure that the border of the object in the corrected DRR 524 does not have double edges, so an exact measurement is possible. In particular, an exact angular measurement 140 and an exact distance measurement 150 can be carried out.

Alternatively, the knowledge of the tilt can be used together with one or more correction functions to computationally correct the true lengths and angles between the measuring point definitions that were created in the uncorrected X-ray image 100. In this case, this can also be carried out by the measurement module according to the invention.

The third advantageous variant that suggests itself is to carry out the measurements directly in the 3D model. For this purpose, distances and angles between predefined landmarks of the 3D objects 300 (transformed and adapted, if applicable) are used, and the Euclidean distances or the distance components referenced to the measurement coordinate system or the output plane 600 are specified. This variant lends itself in particular to mathematically described 3D objects 300 based on the network nodes (for example, with ASM/AAM/SSM).

If long-term storage of the results is desired, the measured values are stored, for example in a database, a PACS or KIS system, or by means of a printable report.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for measuring an X-ray image of an area undergoing medical examination that has at least a first and second object, the method comprising:
    providing a 3D model of an area undergoing examination that includes a first and second virtual 3D object, wherein the first virtual 3D object is to be assigned to the first object to be measured and the second virtual 3D object is to be assigned to the second object to be measured;
    computing a digitally reconstructed X-ray picture based on the 3D model and under an assumption of a virtual projection direction;
    comparing the X-ray image with the digitally reconstructed X-ray picture;
    changing the virtual projection direction relative to the first and second virtual 3D object and at least one of positions of the first and second virtual 3D objects within the 3D model and orientations of the first and second virtual 3D objects relative to one another within the 3D model;
    repeating the steps of comparing and changing until a virtual projection direction, a position of the first and second virtual 3D objects, and a relative orientation of the first and second virtual 3D objects is found in which there is a maximum correlation between the X-ray image and the digitally reconstructed X-ray picture;
    determining a virtual object plane to be assigned to the first and second virtual 3D objects;
    defining a corrected projection direction and an associated output plane that has a known orientation with respect to the virtual object plane determined, the corrected projection direction being oriented orthogonally to the output plane; and
    measuring the X-ray image, taking into account a deviation between the corrected virtual projection direction and the virtual projection direction.

2. The method according to claim 1, wherein the output plane is oriented parallel to the virtual object plane.

3. The method according to claim 1, wherein the output plane is oriented parallel to a principal plane of a coordinate system predefined by the 3D model or by the first and second virtual 3D objects.

4. The method according to claim 1, wherein the step of measuring the X-ray image includes determining a correction function that results from the deviation between the corrected virtual projection direction and the projection direction and applying the correction function to the measurement results.

5. The method according to claim 1, wherein a corrected digitally reconstructed X-ray picture in the output plane is generated based on the corrected virtual projection direction, and wherein the X-ray image is measured using the corrected digitally reconstructed X-ray picture in the output plane.

6. The method according to claim 1, wherein the step of measuring includes a measurement of a distance between measuring points, a measurement of an angle between measuring lines, and/or a measurement of a surface area of measuring areas.

7. The method according to claim 1, wherein the first and second virtual 3D objects are obtained by a method for three-dimensional imaging or by computed tomography or magnetic resonance imaging.

8. The method according to claim 7, wherein the virtual object plane is determined based on the first and second virtual 3D objects using gray-scale intensities assigned to the first and second virtual 3D objects, wherein the virtual object plane is determined based on an optimization or a least squares optimization of a distance between points, lines, curves, or planes, and a selection of voxels of the first and second virtual 3D objects, and/or is determined based on edges or surfaces of the first and second virtual 3D objects and/or with machine learning methods or with trained neural networks.

9. The method according to claim 1, wherein the first and second virtual 3D objects are based on a computer-generated geometry description or on a statistical shape model, an active appearance model, or an active shape model.

10. The method according to claim 9, wherein the virtual object plane is determined based on landmarks associated in advance with the first and second virtual 3D objects.

11. The method according to claim 9, wherein the first and second virtual 3D objects are additionally modified through local and/or elastic deformation.

12. The method according to claim 1, wherein a virtual object plane to be assigned to the majority of virtual 3D objects is determined, and wherein the positions determined in the repeating step of the first and second virtual 3D objects within the 3D model and/or the orientations of the first and second virtual 3D objects relative to the corrected projection direction are taken into account.

13. The method according to claim 12, wherein the measuring step includes the measurement of a distance between two measuring points and/or the measurement of an angle between two measuring lines, and wherein the two measuring points and/or measuring lines are to be assigned to the first and second virtual 3D objects.

14. The method according to claim 1, wherein a scale of length of the 3D model is transferred to the X-ray image.

15. A device for carrying out the method according to claim 1 in which the X-ray image of the area undergoing medical examination that has at least the first and second object, the device comprising:
    a memory, in which the 3D model of the area undergoing examination is stored, wherein the 3D model includes the first and second virtual 3D object, wherein the first virtual 3D object is to be assigned to the first object and the second virtual 3D object is to be assigned to the second object;
    a computing module that is designed to compute the digitally reconstructed X-ray picture using the 3D model and under the assumption of the virtual projection direction;
    a comparison module for comparing the X-ray image with the digitally reconstructed X-ray picture;
    a change module, which is designed to change the virtual projection direction relative to the first and second virtual 3D object and at least one of the positions of the first and second virtual 3D objects within the 3D model, the orientations of the first and second virtual 3D objects relative to one another and the shape of the 3D objects;
a geometry module, which is designed to determine a virtual object plane to be assigned to the first and second virtual 3D objects and to define an output plane that has a known orientation to the virtual object plane and is oriented orthogonally to a corrected projection direction; and
a measurement module for measuring the X-ray image, taking into account the deviation between the corrected virtual projection direction and the virtual projection direction determined and/or taking into account the positions of the first and second virtual 3D objects within the 3D model determined and/or the orientations of the first and second virtual 3D objects relative to the corrected projection direction.

16. A computer program for measuring an X-ray image of an area undergoing medical examination, the computer program comprising computer program code for carrying out the method according to claim 1.

17. The computer program according to claim 16, wherein the computer program is stored on a machine-readable medium or a non-transitory computer readable media.

18. An X-ray measuring system comprising:
an X-ray source that emits X-radiation along a projection direction onto an area undergoing examination that has at least a first and second object;
an X-ray detector detecting an X-ray image produced in an image plane;
a memory adapted to store a 3D model of the area undergoing examination, the 3D model including a first and second virtual 3D object, wherein the first virtual 3D object is to be assigned to the first object and the second virtual 3D object is to be assigned to the second object; and
a display,
wherein a digitally reconstructed X-ray picture is computed using the 3D model and based on a virtual projection direction,
wherein the X-ray image is compared with the digitally reconstructed X-ray picture,
wherein the virtual projection direction is changed relative to the first and second virtual 3D object and at least one of positions of the first and second virtual 3D objects within the 3D model, orientations of the first and second virtual 3D objects or a shape of the 3D object is changed,
wherein a virtual object plane that is to be assigned to the first and second virtual 3D objects is determined,
wherein an output plane is defined that has a known orientation to the virtual object plane and is oriented orthogonally to a corrected projection direction, and
wherein a measurement result is determine based on the X-ray image measured based on a deviation between the corrected virtual projection direction and the virtual projection direction determined or the position of the first and second virtual 3D objects within the 3D model determined or the orientation of the first and second virtual 3D objects relative to the corrected projection direction, and
wherein the measurement result is provided on the display.

* * * * *